(12) United States Patent
Deischinger et al.

(10) Patent No.: US 7,433,504 B2
(45) Date of Patent: Oct. 7, 2008

(54) USER INTERACTIVE METHOD FOR INDICATING A REGION OF INTEREST

(75) Inventors: Harald Deischinger, Frankenmarkt (AT); Petra Hobelsberger, Eberschwang (AT); Walter Duda, Lebertsham (AT)

(73) Assignee: General Electric Company, Schenectady, NY (US)

( * ) Notice: Subject to any disclaimer, the term of this patent is extended or adjusted under 35 U.S.C. 154(b) by 748 days.

(21) Appl. No.: 10/928,944

(22) Filed: Aug. 27, 2004

(65) Prior Publication Data

US 2006/0058605 A1    Mar. 16, 2006

(51) Int. Cl.
*G06K 9/00* (2006.01)
*G06K 9/40* (2006.01)

(52) U.S. Cl. .................. 382/128; 382/254; 382/129; 382/130; 382/131; 382/132

(58) Field of Classification Search .................. None
See application file for complete search history.

(56) References Cited

U.S. PATENT DOCUMENTS

| | | | |
|---|---|---|---|
| 5,048,099 A * | 9/1991 | Lee | 382/175 |
| 5,570,430 A | 10/1996 | Sheehan et al. | |
| 5,790,216 A | 8/1998 | Inbar et al. | |
| 6,081,611 A * | 6/2000 | Linford et al. | 382/128 |
| 6,111,588 A * | 8/2000 | Newell | 345/442 |
| 6,327,393 B1 * | 12/2001 | Bruder | 382/256 |
| 6,429,861 B1 | 8/2002 | Hossack et al. | |
| 6,484,048 B1 | 11/2002 | Hoshino et al. | |
| 6,542,153 B1 | 4/2003 | Liu et al. | |
| 6,724,938 B1 | 4/2004 | Matsumura | |
| 6,775,399 B1 | 8/2004 | Jiang | |
| 7,170,517 B2 * | 1/2007 | Raman et al. | 345/424 |
| 2001/0056234 A1* | 12/2001 | Weinberg | 600/436 |
| 2003/0016852 A1* | 1/2003 | Kaufman et al. | 382/131 |
| 2003/0052879 A1* | 3/2003 | Barth et al. | 345/424 |
| 2004/0091084 A1* | 5/2004 | Griffith | 378/210 |

* cited by examiner

*Primary Examiner*—Brian Q Le
*Assistant Examiner*—Michelle Entezari
(74) *Attorney, Agent, or Firm*—The Small Patent Law Group; Dean D. Small (57) ABSTRACT

A method for defining a volume of interest (VOI) in a medical image is presented. A user interface is used to select a point on an initial linear border segment of a volume of interest. The user drops the point at a new position and a processor forms a new, non-linear border segment which includes the point. A 3D presentation of the volume of interest is created.

9 Claims, 12 Drawing Sheets

USER INTERACTIVE METHOD FOR INDICATING A REGION OF INTEREST

BACKGROUND OF THE INVENTION

This invention relates generally to medical imaging systems. In particular, the present invention relates to method and apparatus for defining a region of interest in a medical image.

Various methods are available for drawing the contour of an object, within a medical image. For example, the object may be a fetus, organ, cyst, or tumor which the user is interested in further analyzing. The area enclosed by the contour represents the "region of interest" (ROI) of the image. Typically the user is uninterested in the other features shown on the image and selecting a ROI allows the user to concentrate the processor power of the system on the part of the image which is of most interest to the user.

Problems exist with the current methods for selecting the border segments of a ROI. For example, one method is to employ known shapes, such as rectangles, circles and ovals, then require the user to drag the contour of the shape to the desired location around the object. Still another method has the user draw the contour of the object using a mouse or various keyboard keys, which can be quite time consuming, with accuracy being affected by the display size and resolution, and the minimum distance the user may move the cursor on the display. Also, working with 3D images adds an additional element of complexity.

Thus, a method is desired to obtain the border segments of a ROI within an image that addresses the problems noted above and others previously experienced.

BRIEF DESCRIPTION OF THE INVENTION

In one embodiment, a method for displaying a ROI within an image comprises a user interface for defining an initial ROI within said image by surrounding said ROI with linear border segments wherein said user interface is adapted to allow a user to redefine said initial ROI by replacing at least one of said linear border segments with a non-linear border segment to form a new ROI which differs art least partially from the initial ROI.

In one embodiment, a method for displaying a ROI within an image comprises a user interface for defining an initial ROI within said image by surrounding said ROI with linear border segments arranged to form a rectangle wherein said user interface is adapted to allow a user to redefine said initial ROI by replacing at least one of said linear border segments with a non-linear border segment to form a new ROI which differs art least partially from the initial ROI.

DETAILED DESCRIPTION OF THE INVENTION

Figure 1:
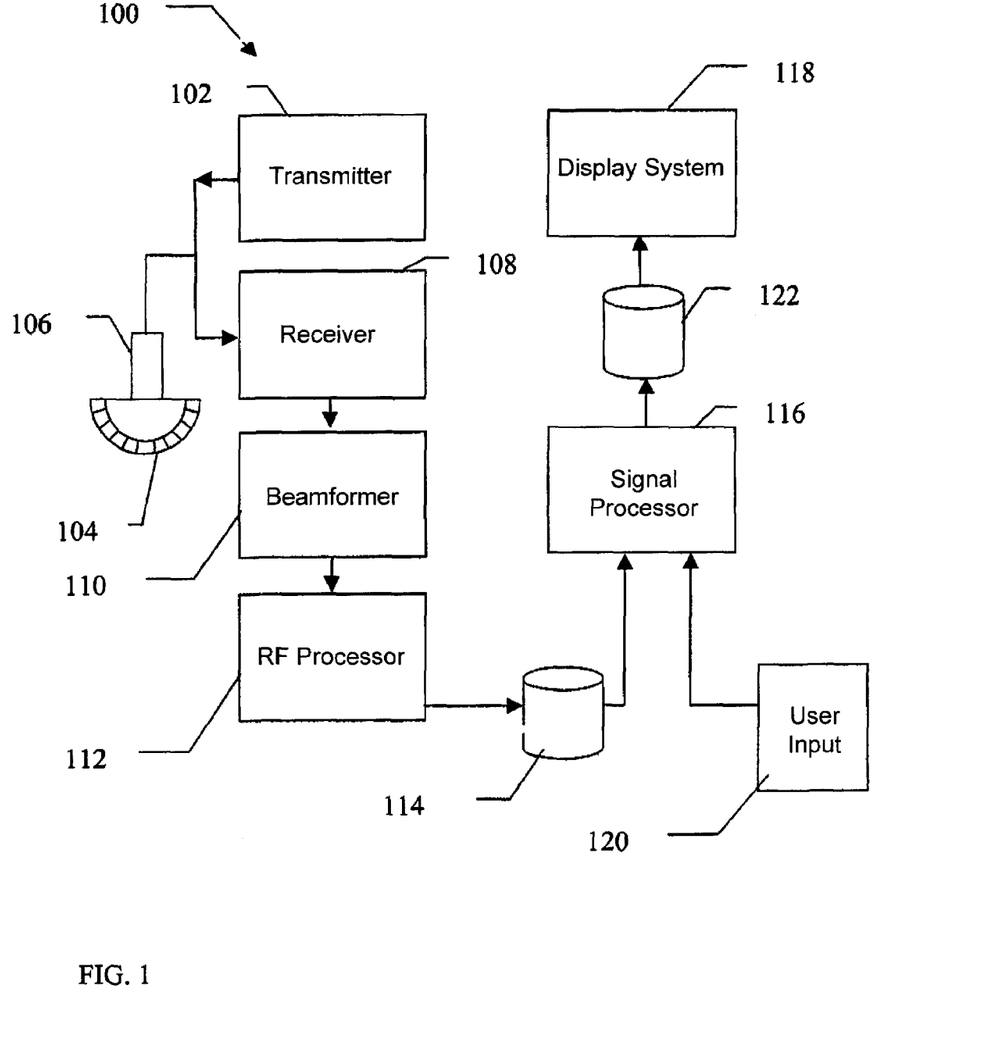
FIG. 1 illustrates a block diagram of an ultrasound system formed in accordance with an embodiment of the present invention.

FIG. 1 illustrates a block diagram of an ultrasound system 100 formed in accordance with an embodiment of the present invention. The ultrasound system 100 includes a transmitter 102 which drives elements 104 within a transducer 106 to emit pulsed ultrasonic signals into a body. A variety of geometries may be used. The ultrasonic signals are back-scattered from structures in the body, like blood cells or muscular tissue, to produce echoes which return to the elements 104. The echoes are received by a receiver 108. The received echoes are passed through a beamformer 110, which performs beamforming and outputs an RF signal. The RF signal then passes through an RF processor 112. Alternatively, the RF processor 112 may include a complex demodulator (not shown) that demodulates the RF signal to form IQ data pairs representative of the echo signals. The RF or IQ signal data may then be routed directly to RF/IQ buffer 114 for temporary storage. A user input 120 may be used to input patient data, scan parameters, a change of scan mode, and the like.

The ultrasound system 100 also includes a signal processor 116 to process the acquired ultrasound information (i.e., RF signal data or IQ data pairs) and prepare frames of ultrasound information for display on display system 118. The signal processor 116 is adapted to perform one or more processing operations according to a plurality of selectable ultrasound modalities on the acquired ultrasound information. Acquired ultrasound information may be processed in real-time during a scanning session as the echo signals are received. Additionally or alternatively, the ultrasound information may be stored temporarily in RF/IQ buffer 114 during a scanning session and processed in less than real-time in a live or off-line operation.

The ultrasound system 100 may continuously acquire ultrasound information at a frame rate that exceeds 50 frames per second—the approximate perception rate of the human eye. The acquired ultrasound information is displayed on the display system 118 at a slower frame-rate. An image buffer 122 is included for storing processed frames of acquired ultrasound information that are not scheduled to be displayed immediately. Preferably, the image buffer 122 is of sufficient capacity to store at least several seconds' worth of frames of ultrasound information. The frames of ultrasound information are stored in a manner to facilitate retrieval thereof according to its order or time of acquisition. The image buffer 122 may comprise any known data storage medium.

Figure 2:
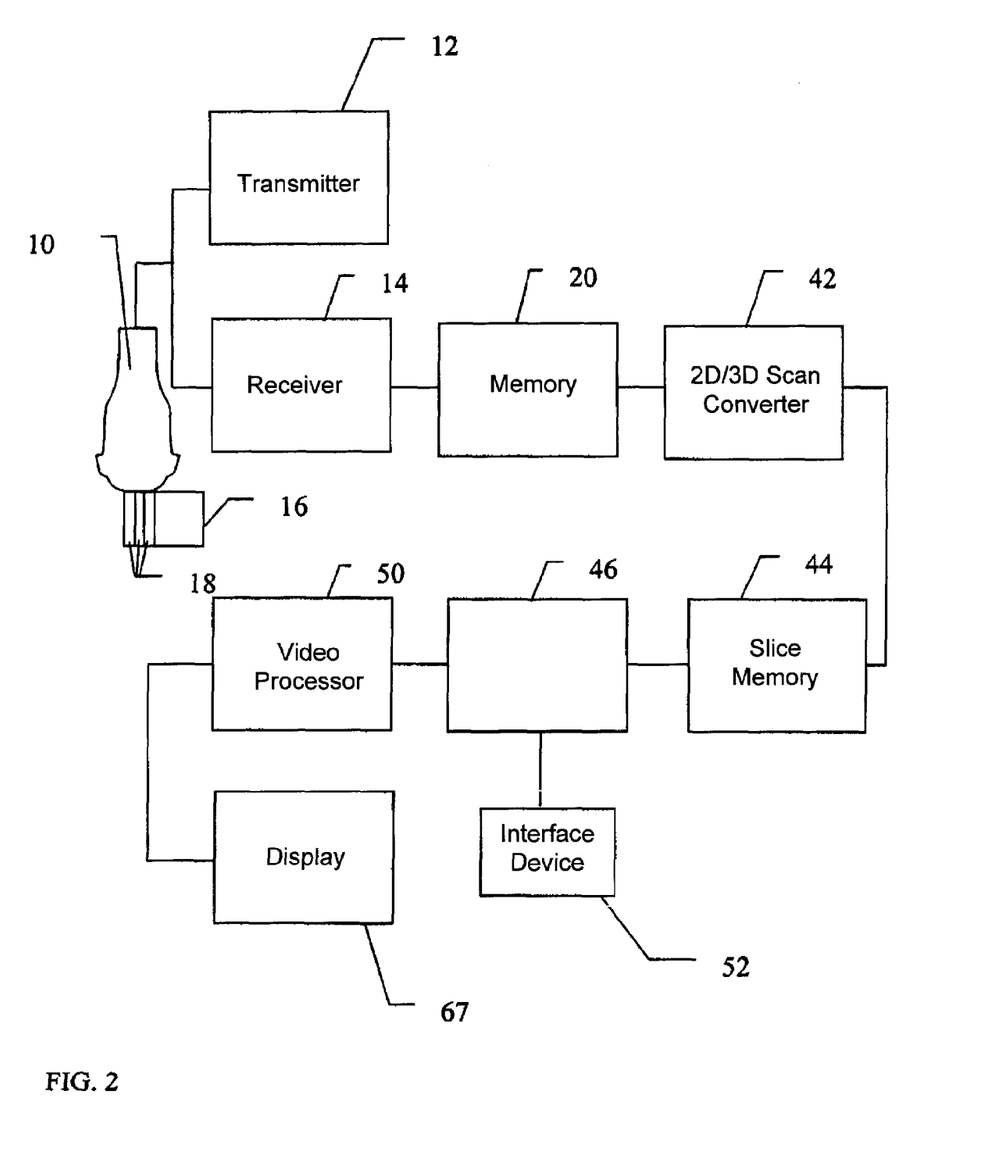
FIG. 2 illustrates an ultrasound system formed in accordance with an embodiment of the present invention.

FIG. 2 illustrates an ultrasound system formed in accordance with one embodiment of the present invention. The system includes a transducer 10 connected to a transmitter 12 and a receiver 14. The transducer 10 transmits ultrasonic pulses and receives echoes from structures inside of a scanned ultrasound image or volume 16. Memory 20 stores ultrasound data from the receiver 14 derived from the scanned ultrasound image or volume 16. The image or volume 16 may be obtained by various techniques (e.g., conventional B-mode scanning, 3D scanning, real-time 3D or 4D imaging, volume scanning, 2D scanning with an array of elements having positioning sensors, freehand scanning using a Voxel correlation technique, 2D or matrix array transducers and the like).

The transducer 10 is moved, such as along a linear or arcuate path, while scanning a volume of interest (VOI). At each linear or arcuate position, the transducer 10 obtains 3D volume data or 2D scan planes 18. The volume data or scan planes 18 are stored in the memory 20, and then passed to a 2D/3D scan converter 42. In some embodiments, the transducer 10 may obtain lines instead of the scan planes 18, and the memory 20 may store lines obtained by the transducer 10 rather than the scan planes 18. The 2D/3D scan converter 42 creates a data slice from the volume data or from single or multiple 2D scan planes 18. The data slice is stored in slice memory 44 and is passed to the video processor 50 and display 67.

The position of each echo signal sample (pixel for scanned image or Voxel for scanned volume) is defined in terms of geometrical accuracy (i.e., the distance from one pixel/Voxel to the next) and ultrasonic response (and derived values from the ultrasonic response). Suitable ultrasonic responses may include gray scale values, color flow values, and angio or power Doppler information, and the like.

Figure 3:
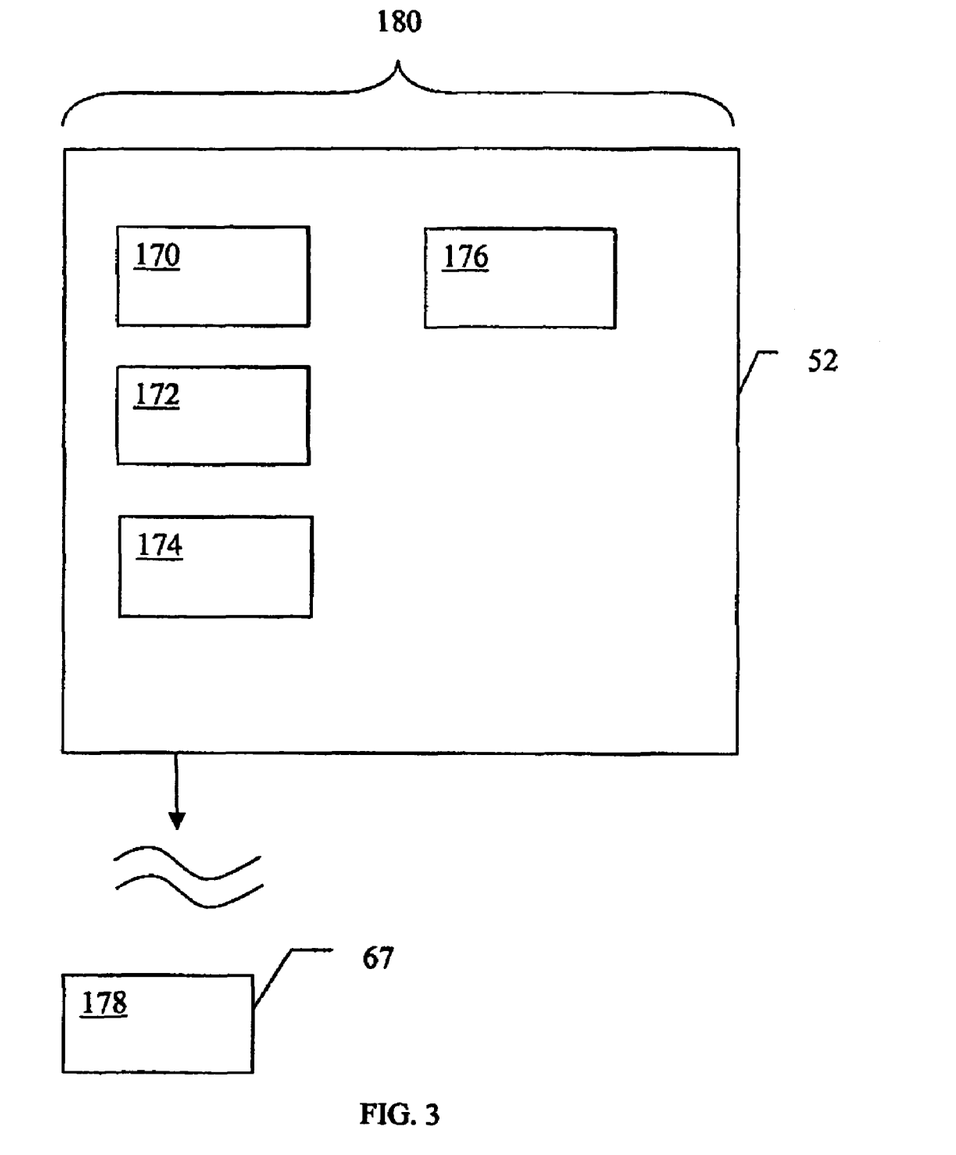
FIG. 3 illustrates the interface devices and display of FIG. 2 in accordance with an embodiment of the present invention.

FIG. 3 illustrates the interface device 52 and display 67 of FIG. 2. The interface device 52 may comprise one or more of a keyboard 170, mouse 172, track ball 174, and touch pad 176. The display 67 may also comprise a touch screen 178. The keyboard 170, mouse 172, track ball 174, touch pad 176 and touch screen 178 will be referred to collectively as interface devices 180. The user may use one or more of the interface devices 180 to interactively select points, areas and/or lines on the display 67.

Figure 4:
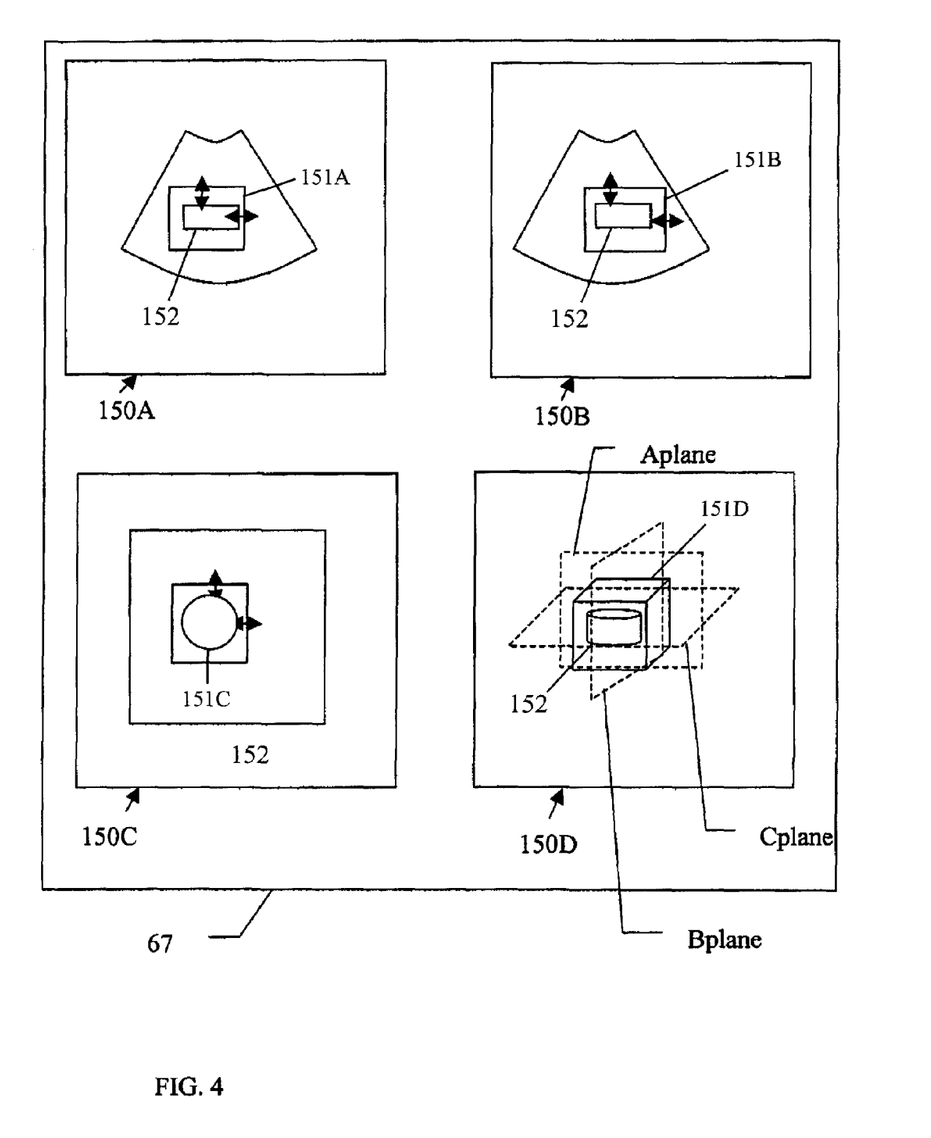
FIG. 4 illustrates orthogonal and 3D images produced by a prior art ultrasound system.

FIG. 4 shows schematically images 150A-150D comprising diagnostic ultrasound data which can be displayed simultaneously or individually on display 67. It should be understood that although the below methods and apparatus are discussed with respect to ultrasound, other diagnostic data may be used, such as, but not limited to, X-ray, MR and CT. The images 150A-150D includes an object 152. By way of example only, the object 152 may be an organ, such as a liver or kidney, a tumor, cyst, blood vessel, and the like. Image 150A represents the ultrasound data from a first plane Aplane, image 150B shows the same data from a second plane Bplane which is orthogonal to the first viewing angle, image 150C shows the same data from a third plane Cplane which is orthogonal to both the first and second viewing angles, and FIG. 150D shows a 3D representation of the same data taken from a viewing angle. Each image 150A-C contains a rectangular region of interest box 151A-151C respectively and image 150D shows a cuboid region of interest volume 151D. Typically each region of interest box 151A-151D is individually user selectable by means of interface device 180 and once a user has selected a box the user is able to change the dimensions of the box as shown by the double headed arrows in FIG. 4. Changes made to the dimensions of a box in one image 150A-150C may be automatically followed by corresponding changes in the other images 150A-150D.

Figure 5:
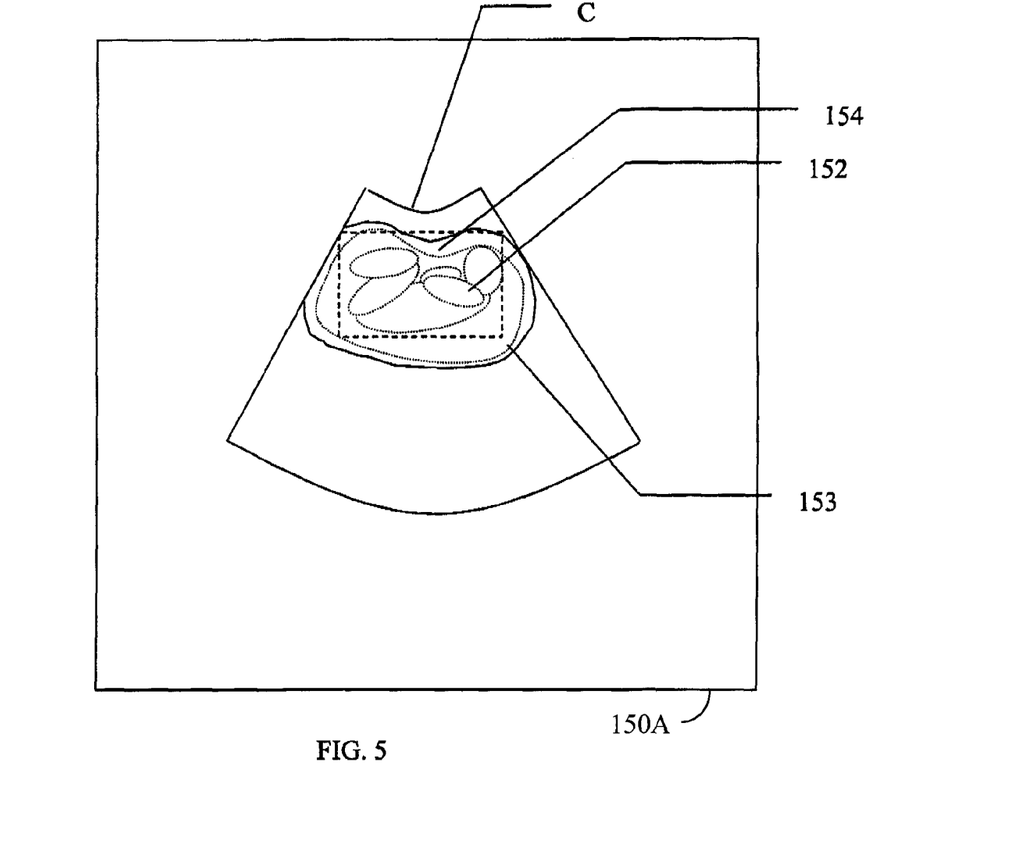
FIG. 5 shows a schematic image of an ultrasound scan.

FIG. 5 shows a view corresponding to image 150A of FIG. 4 in which the object 152 is a fetus inside its mother's womb 153 viewed using a transvaginal probe with a semi-spherical transponder head. It is clear from FIG. 5 that the curvature C of the transponder head is reflected in the images 150A-150D and make it impossible to form a ROI box which completely encloses the object 152 while at the same time excludes the mother's tissue—for example part of the wall of the womb 154.

Figure 6A:
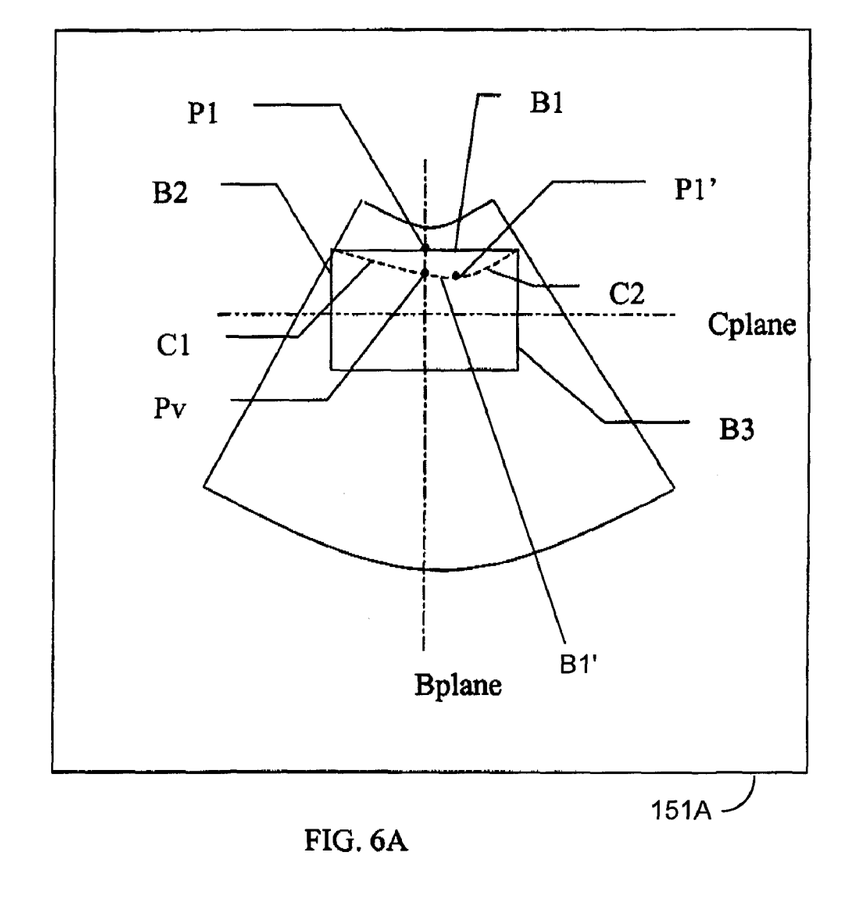
FIG. 6 shows stages in the formation of a new region of interest in accordance with an embodiment of the present invention.
Figure 6B:
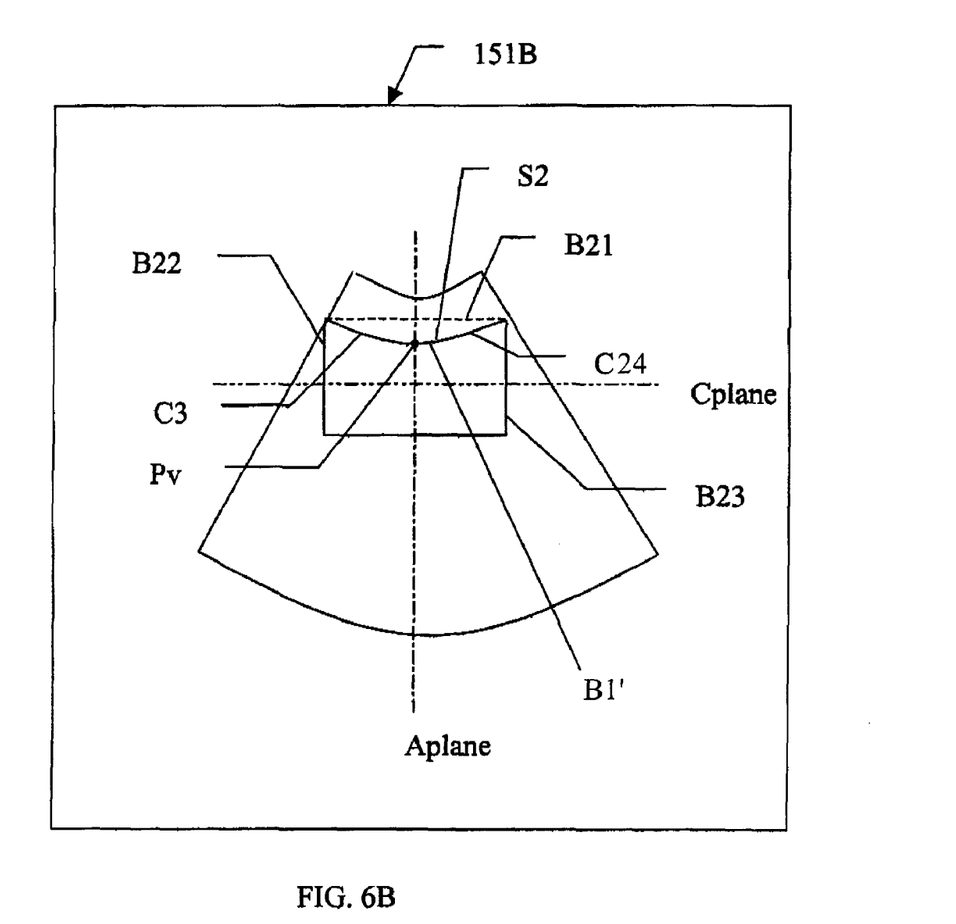
Figure 6C:
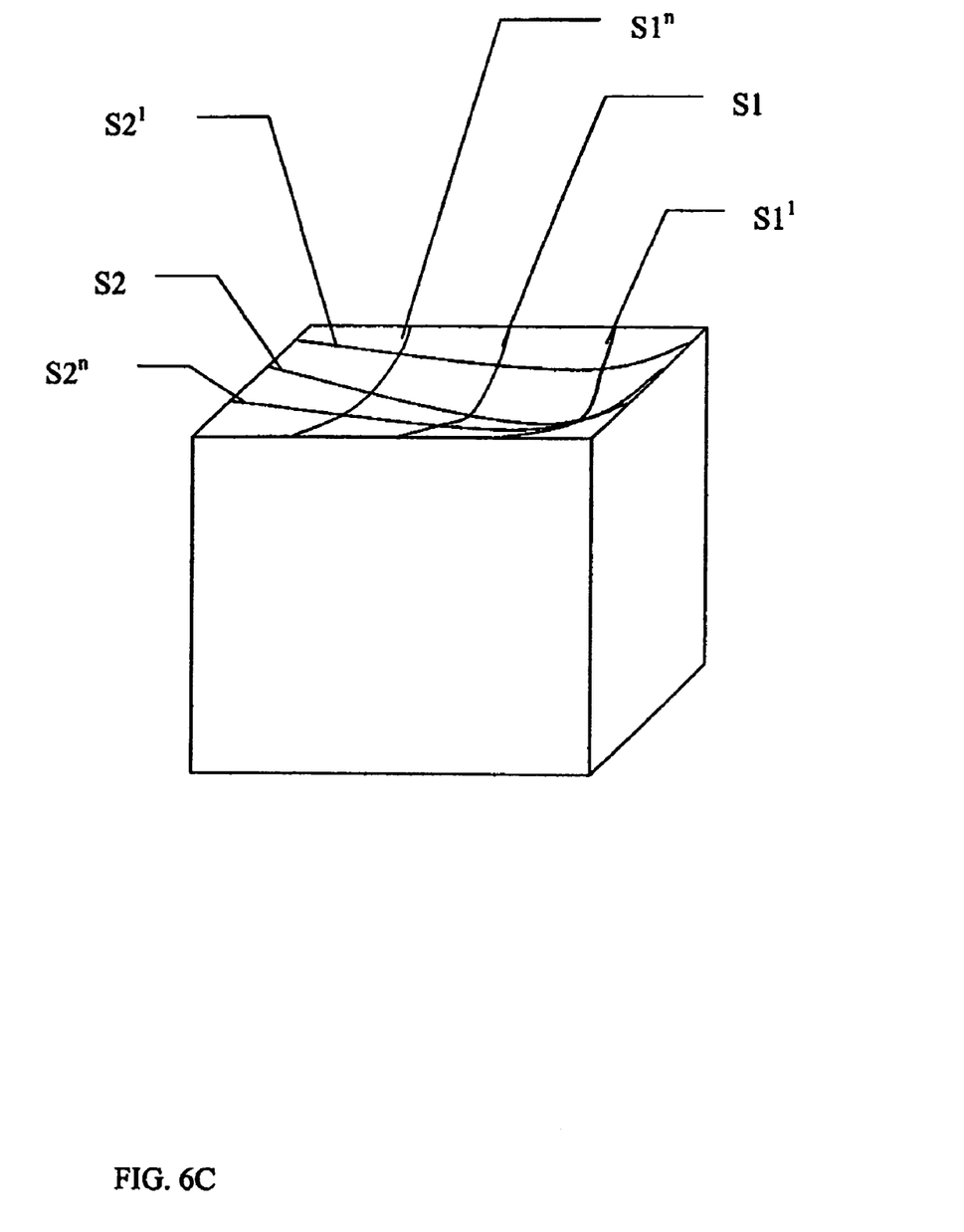

FIG. 6 illustrates an embodiment of a method for redefining the border segments of an initial region of interest box 150A-150C so that the shape of the region of interest box more closely corresponds to that of the contour of the object within the image 150A-150C. The user selects one of the images 150A-150C to work on. In this case, purely as an example, the user starts with image 150A as shown in FIG. 6A in which an initial region of interest box 151A is shown—in this interests of clarity the object of interest is not shown in FIGS. 6A-6C. The linear border segment B1 of the initial region of interest box 151A which the user wishes to modify in this case is the top border segment B1 and this is selected by use of an interface device 180. A point P1 is displayed in the center of the selected border segment B1 by the processor. The user can select the point P1 with the interface device, move it to a new position P1' and drop it there. The processor draws a spline S1 comprised of two smooth curve line segments C1, C2 from point P1'—curve line segment C1 extends to the top end of the vertical left hand border segment B2 of the region of interest box 151A and curve line segment C2 extends to the top end of the vertical right hand border segment B3 of the region of interest box 151A. Curve line segments C1 and C2 form the new border segment B1' of region of interest box 151A. At the same time the processor calculates a virtual point Pv which is where the new border segment B1' passes though the plane Bplane of the image 151B and displays this point on image 151B along with a spline S2 comprised of two curve line segments C3 and C4. Spline S2 replaces the originally linear top border B21 of image 151B. Curve line segment C3 extends from Pv to the top end of the vertical left hand border segment B22 of the region of interest box 151A and curve line segment C24 extends to the top end of the vertical right hand border segment B23 of the region of interest box 151A as shown in FIG. 6B. The processor also redraws the 3D presentation of the region of interest volume as shown in FIG. 6C by producing further splines $S1^1$-$S1'''$ parallel to S1 and $S2^1$-$S2'''$ parallel to S2. These splines $S1^1$-$S1'''$, $S2^1$-$S2'''$ are attached to curve line segments C1-C2 and C3-C4 respectively.

Figure 7A:
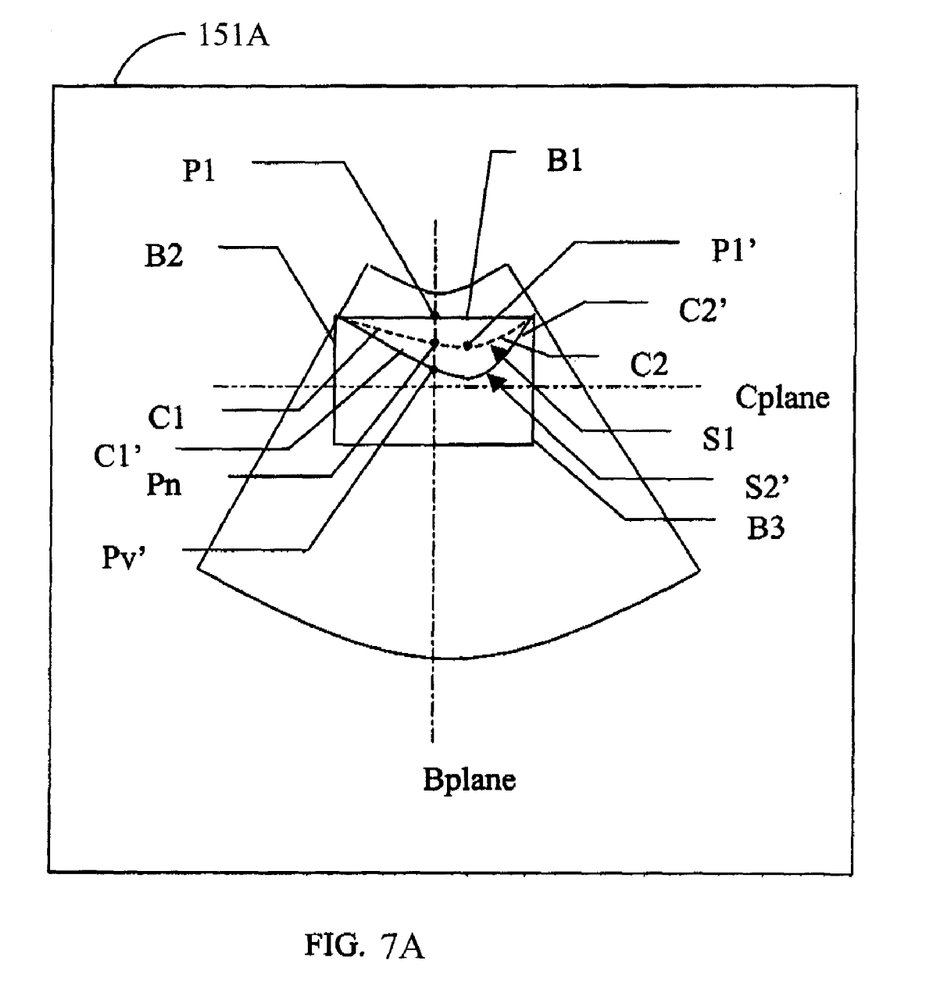
FIG. 7 shows stages in the formation of a new region of interest in accordance with another embodiment of the present invention.
Figure 7B:
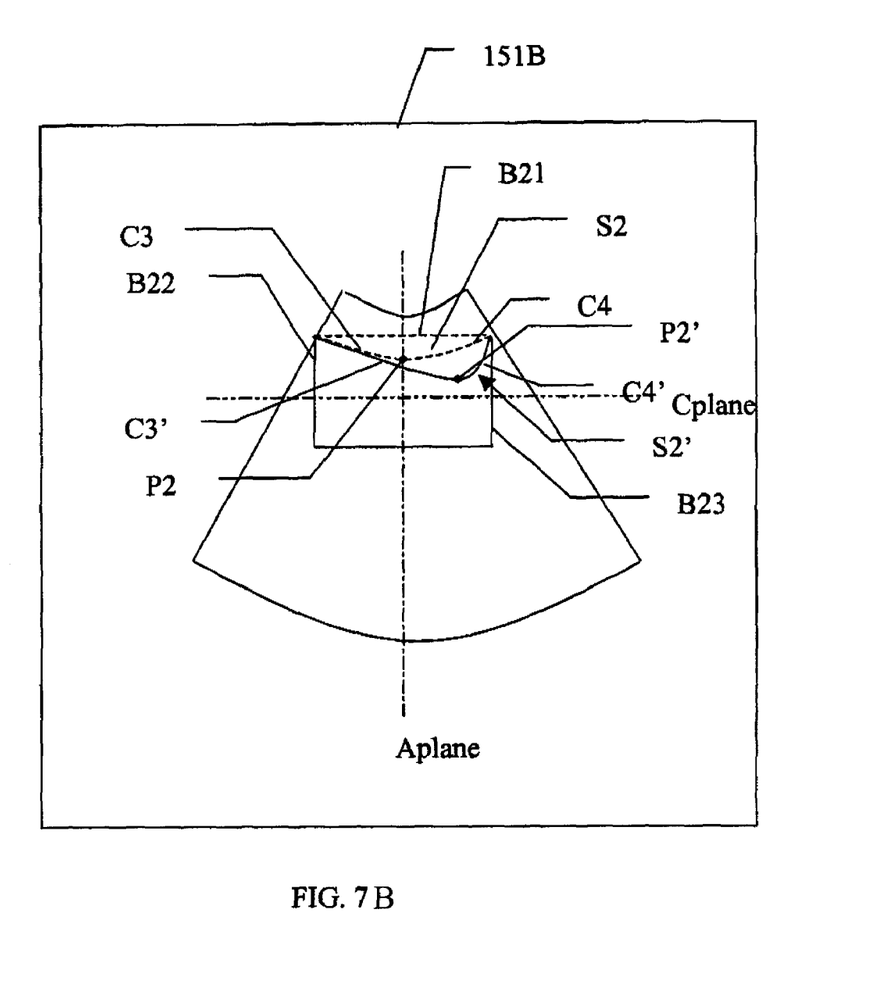
Figure 7C:
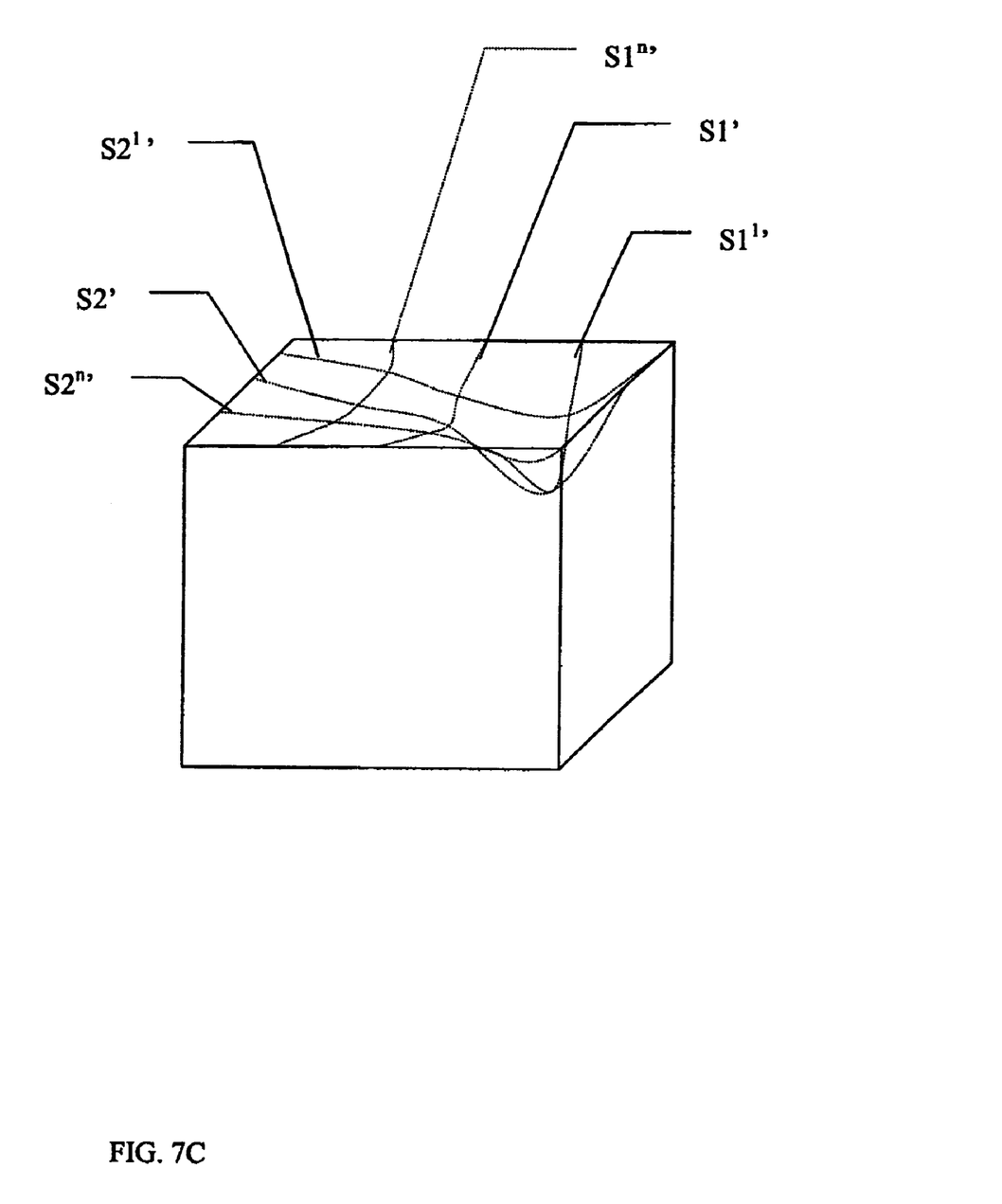

FIGS. 7A-7C illustrates a second embodiment of a method for redefining the border segments of a region of interest, in which, after the user has moved point P1 to position P1' in image 151A, the user is provided with the possibility of moving a point P2 in the image 151B to a new position P2' and dropping it there. The processor draws a new spline S2' which is made of two smooth curve line segments C3', C4' and which replaces spline S2. At the same time the processor calculates a virtual point Pv' which is where the new spline S2' passes though the plane Aplane of the image 151A and displays this point on image 151A along with a spline S1' comprised of two curve line segments C1' and C2'. Curve line segments C1' and C2' may be formed by the calculating the distance between Pv' and the point Pn vertically above it on spline S1, calculating what a proportion this distance is of the distance between Pn and the point e.g. P1 vertically above on the original border segment B1 and moving all the points on lines C1 and C2 by the same proportion of their respective vertical distances from original border segment B1. For example if the distance between Pv' and Pn is 100% of the distance between Pn and P1 then all the points on C1 and C2 are moved a further 100% of their distances from border segment B1 to form curved lines C1' and C2'. Spline S1' replaces spline S1. The processor also redraws the 3D presentation of the region of interest volume as shown in FIG. 7C by producing further splines $S1^{1'}$-$S1'''$ parallel to S1' and $S2^{1'}$-$S2'''$ parallel to S2'. These splines $S1^{1'}$-$S1'''$, $S2'$-$S2'''$ are attached to curve line segments C1'-C2' and C3'-C4' respectively.

Figure 8:
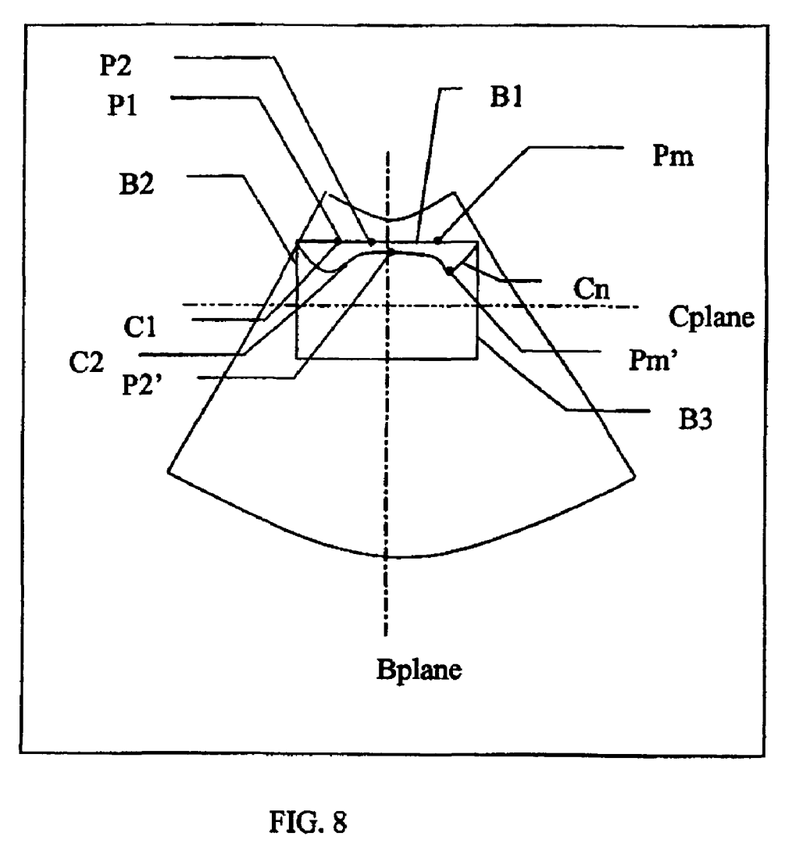
FIG. 8 shows stages in the formation of a new region of interest in accordance with a further embodiment of the present invention.

In a further embodiment of a method for redefining the border segments of a region of interest, illustrated in FIG. 8 the user is permitted to move a plurality of points P1a-P1m in an image to new positions P1a'-P1m' in order to produce a border segment B1' comprised of an n-order curve comprising curve line segments C1-Cm.

In another embodiment of a method for redefining the border segments of a region of interest, the user is permitted to modify the linear boundary segments of more than one side of an initial region of interest box.

While the invention has been described in terms of various specific embodiments, those skilled in the art will recognize that the invention can be practiced with modification within the spirit and scope of the claims.

What is claimed is:

1. A method for defining a volume of interest (VOI) in a medical image, comprising:
    displaying a medical image representative of anatomical structure;
    defining an initial VOI within said image by surrounding said initial VOI with linear border segments;
    moving a point on a said linear border segment;
    using the moved point on the linear border segment to replace at least one said linear border segment with curved line segments to create a new border segment and creating a virtual point at which the new border segment passes through another planar view of the medical image;
    moving the virtual point in the other planar view of the medical image; and
    using the moved point, the virtual point, and splines in parallel planes to redraw a 3D presentation of the VOI with a curved surface.

2. The method of claim 1, further comprising moving the point on the linear border segment through a user interface.

3. The method of claim 1, further comprising presenting the point to be moved on said linear border segment, and identifying a final location of the moved point on the linear border segment said non-linear border segment being placed on said medical image based on said final location of said moved point on the linear border segment.

4. The method of claim 1, wherein said non-linear border segment includes at least one of linear partial segments, and n-th order curved line segments, where n is at least two.

5. The method of claim 1, wherein said includes replacing a plurality of said linear border segments with non-linear border segments.

6. A system for defining a volume of interest (VOI) in a medical image, comprising;
    a display configured to display a medical image representative of anatomical structure;
    a processor configured to define an initial VOL within said image by surrounding said initial VOI with linear border segments; and
    a user interface configured to accept user input to move a point on a said linear border segment;
    said processor further configured to use the moved point on the linear border segment to replace at least one said linear border segment with curved line segments to create a new border segment and to display on said display a virtual point at which the new border segment passes through another planar view of the medical image;
    said user interface further configured to accept user input to move the virtual point in the other planar view of the medical image; and
    said system configured to use the moved point, the virtual point, and splines in parallel planes to redraw a 3D presentation of the VOI with a curved surface.

7. The system of claim 6, wherein said user interface includes at least one of a trackball, a mouse, and a keyboard.

8. The system of claim 6, wherein said processor is configured to present said point to be moved on the linear border segment and to place said new border segment on said medical image based on a final location of said moved point.

9. The system of claim 6, wherein said new border segment includes n-th order curved line segments, where n is at least two.

* * * * *